United States Patent [19]
Davini

[11] Patent Number: 5,385,537
[45] Date of Patent: Jan. 31, 1995

[54] SPLINT SYSTEM

[76] Inventor: Mark A. Davini, 382 Boston Turnpike, Suite 101, Shrewsbury, Mass. 01545

[21] Appl. No.: 987,376

[22] Filed: Dec. 8, 1992

[51] Int. Cl.6 ................................. A61F 5/04
[52] U.S. Cl. ........................ 602/21; 602/20; 128/878
[58] Field of Search ............ 602/21, 22, 20, 23, 602/5, 6; 128/876, 877, 878, 879

[56] References Cited

U.S. PATENT DOCUMENTS

| | | | |
|---|---|---|---|
| 3,124,127 | 3/1964 | Ruuska | 602/21 |
| 3,299,887 | 1/1967 | Czap | 602/21 |
| 4,662,364 | 5/1987 | Viegas | 602/21 |
| 4,677,971 | 7/1987 | Lindemann | 602/21 |
| 4,854,309 | 8/1989 | Elsey | 602/21 |
| 4,966,137 | 10/1990 | Davini | 602/21 |
| 5,160,314 | 11/1992 | Peters | 602/21 |

Primary Examiner—Robert A. Hafer
Assistant Examiner—David J. Kenealy

[57] ABSTRACT

Improved splint system including a brace and attached strap for use in the treatment and prevention of carpal tunnel syndrome.

8 Claims, 1 Drawing Sheet

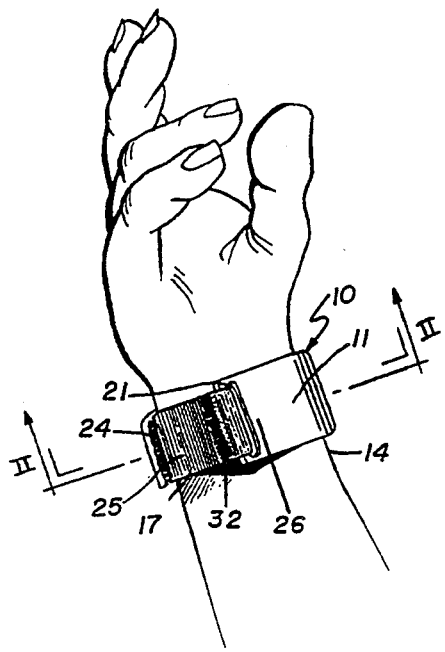
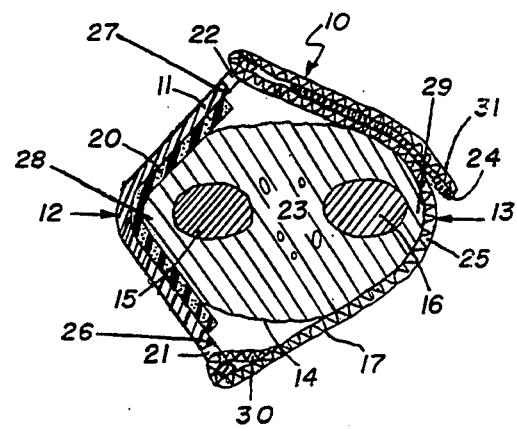
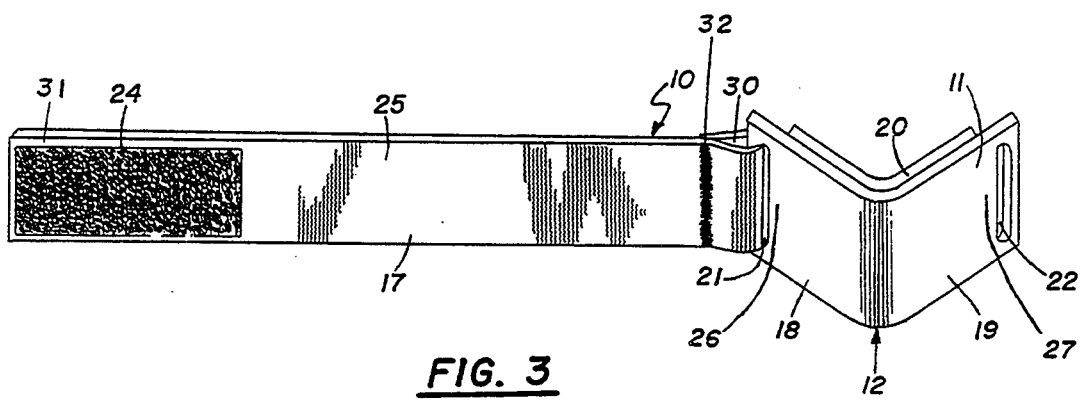

SPLINT SYSTEM

BACKGROUND OF THE INVENTION

One of the most difficult problems encountered by health care providers is the successful treatment of the so-called "carpal tunnel syndrome". This syndrome is defined as a median nerve compression neuropathy at the volar (palmar) aspect of the wrist where the nerve passes beneath the transverse carpal ligament. In general, carpal tunnel syndrome occurs when the median nerve is compressed as it passes through a narrow tunnel of bone and ligaments at the wrist. This median nerve conducts sensation from part of the hand, up the arm, to the central nervous system. When the nerve is compressed, the result is numbness, tingling, burning and pain in the fingers and the hand. Some of the causes of carpal tunnel syndrome include nerve compression when the lubricating lining around the tendons becomes thick and sticky due to the normal wear and tear of aging, or from repetitive hand movements, thus pressing the nerve against the tunnel. Another cause is bone dislocation and fracture due to previous dislocation or fracture of the wrist, causing bone to protrude into the tunnel and press against the nerve. Arthritis may also be present and consequently the tunnel becomes too narrow and puts pressure on the nerve. Another cause of the syndrome is fluid retention which causes swelling of the tissue in the carpal tunnel including, perhaps, the nerve itself. This occurs most often during pregnancy with the symptoms subsiding after the baby is born. Since the space in the carpal tunnel is limited, the injury to the structures is further aggravated by friction with other elements in the tunnel. The carpal tunnel is formed by the anterior concavity of the carpal bones and the flexor retinaculum (transverse carpal ligament). It is a space that has a cross-section that is approximately oval-shaped. This space is almost completely occupied by flexor tendons and the median nerve so that there is very little extra space when an injury occurs. The result is, therefore, that in this tightly constricted space, the median nerve and tendons further injure themselves by rubbing against each other. Prescribed treatment for the syndrome is, in general, to allow the swollen structures to heal up and thereby have its swelling reduced. However, since the hand is in use at all times and the structures move back and forth as the fingers and hand are articulated, it is difficult not to re-irritate the injured structures. Therefore, in the past, the treatment has been to provide a fixation of the important parts of the hand that cause the structures to move through the tunnel. The immobilization has been accomplished by the use of splints such as the "cockup splint" or by the use of a band tightly wrapped around the wrist. The inadequacies of both of these splints are that they limit the use of the hand which is being treated, they do nothing to support the normal biomechanics of the wrist, and they compress the anterior surface and, thereby, allow for further injury. U.S. Pat. No. 4,966,137 to Davini (the inventor of the present invention) presents a splint which obviates these and other difficulties that existed in prior art devices. The embodiment of the splint presented in the earlier Davini patent, while very effective, has a number of practical drawbacks. It involves a number of individual parts. It also requires a significant amount of material. Furthermore, the device must be provided in a number of sizes in order to adapt to various wrist sizes. Finally, the device can be somewhat difficult to apply and somewhat conspicuous in use.

It is, therefore, a principal object of the present invention to provide an improved splint system which gives improved successful treatment of carpal tunnel syndrome.

Another object of the invention is to provide an improved splint system for the prevention of carpal tunnel syndrome.

A further object of the invention is to provide an improved splint system for the treatment and prevention of carpal tunnel syndrome without requiring immobilization of the hand and fingers.

A further object of the invention is to provide an improved splint system for the treatment and prevention of carpal tunnel syndrome, which system can be worn during many activities that commonly cause the syndrome.

A further object of the invention is to provide an improved splint system for the treatment and prevention of carpal tunnel syndrome, which system maintains and/or restores the size and shape of the carpal tunnel, thus allowing decompression of the involved injured structures and maintenance of normal structural relationships.

A further object of the invention is to provide an improved splint system for the treatment and prevention of carpal tunnel syndrome, which system can be readily removed by the patient for washing and the like.

A further object of the invention is to provide an improved splint system for the treatment and prevention of carpal tunnel syndrome in which the components of the system are constructed so as to form a unitary device, at least at the time of application of the system, instead of a device with more than one individual part.

A further object of the invention is to provide an improved splint system for the treatment and prevention of carpal tunnel syndrome, which system is simple in construction, inexpensive to manufacture, and capable of a long life of useful service with a minimum of maintenance.

A further object of the invention is to provide an improved splint system for the treatment and prevention of carpal tunnel syndrome, which system can be readily applied without the use of special equipment.

A further object of the invention is to provide an improved splint system for the treatment and prevention of carpal tunnel syndrome, which system can fit a wide range of wrist sizes.

SUMMARY OF THE INVENTION

In general, the invention consists of a brace formed of semi-rigid material which exteriorly cradles either the radius or the ulna in the wrist of a human being. The brace is held in place by an attached flexible strap which embraces the other of the two bones. The brace and strap act to approximate the radius and ulna toward one another to support the carpal tunnel without allowing compression of the anterior surface of the carpal tunnel.

More specifically, the brace is made of semi-rigid material and has a V-shaped cross section. In the preferred embodiment, a cushion is adhered to the inside surface of the brace so that the cushion and not the brace comes in direct contact with the human being's skin.

BRIEF DESCRIPTION OF THE DRAWINGS

FIG. 1 is a perspective view of an improved splint system embodying the principles of the present invention, shown in use with a human arm;

FIG. 2 is a vertical cross-sectional view taken along line II—II in FIG. 1 and looking in the direction of the arrows; and FIG. 3 is a perspective view of the improved splint system.

DESCRIPTION OF THE PREFERRED EMBODIMENT

Referring to the drawings, it can be seen that the improved splint system, indicated generally by the reference number 10, includes a flexible elongated strap 17 and a brace 11. In FIG. 3, it can be seen that the brace 11 has a V-shaped cross section having adjacent sides 18 and 19 which are joined by a rounded corner 12. The strap 17 is joined with the brace 11, either permanently or removably. In the permanent mode, a first free end 30 of the strap 17 is inserted through a small opening 21 on a first free end 26 of the brace 11 and affixed to itself as shown in FIGS. 1 and 3 by stitching 32 or the like. In the removable mode, the first free end 30 of the strap 17 is inserted through the small opening 21 on the first free end 26 of the brace 11 and affixed to itself by a snap or the like. The strap 17 has a second free end 31 which extends through a small opening 22 on a second free end 27 of the brace 11 and is fastened to itself by means of a hook-and-loop system of the type sold under the trademark "VELCRO" consisting of a hook portion 24 and a loop portion 25. The strap 17 and brace 11 are shown in FIG. 1 in place on the wrist 14 of a person, for the treatment or prevention of carpal tunnel syndrome.

Referring to FIG. 2, it can be seen that the improved splint system 10, used for the treatment and prevention of carpal tunnel syndrome, includes the brace 11 and the strap 17. The brace 11 exteriorly cradles the radius 15 in the wrist 14 of the person and is shown in cross-section along with the ulna 16. The brace 11 is formed of a semi-rigid material, such as a thermoplastic resin, and has a V-shaped cross section. In the preferred embodiment, the splint system 10 includes a cushion 20 which is formed from a generally rectangular sheet of a resilient polymeric material approximately ⅛" in diameter. The cushion 20 is adhered to the inside surface of the brace 11 so that the cushion 20 and not the brace 11 comes in direct contact with the person's skin. The cushion 20 is somewhat smaller in size than the brace 11 so that the openings 21 and 22 on the first free end 26 and the second free end 27, respectively, of the brace 11 are not obstructed. While the brace 11 exteriorly cradles the radius 15 at corner 12 at a first narrow side 28 of the wrist 14, the fastened strap 17 exteriorly embraces the ulna 16 at edge 13 at a second narrow side 29 of the wrist 14 to approximate the two bones toward one another. When placed on the wrist of a person requiring treatment for or prevention of carpal tunnel syndrome, the second free end 31 of the strap 17 is inserted through the small opening 22 on the second free end 27 of the brace 11 on side 19 and is fastened to itself by the hook portion 24 and the loop portion 25.

The operation of the invention will now be readily understood in view of the above description. The brace 11 is placed on a person's wrist 14 to exteriorly surround the radius 15. The strap 17 is then exteriorly wrapped around the ulna 16 and is pulled enough to cause a proper support of the wrist 14 and to cause a slight approximation of the radius 15 and the ulna 16 toward one another. Since the carpal tunnel (indicated generally by the reference numeral 23) lies between these two bones and contains the tendons and nerves, etc. that cause the problem in the carpal tunnel syndrome, the effect is to support the tunnel by maintaining or restoring its normal dimension in a line perpendicular to a line joining the centers of the ulna 16 and the radius 15. This relieves any pressure that may exist in the carpal tunnel 23 and allows the injured element to heal. At the same time that healing is taking place, the fact that the carpal tunnel dimension has been supported in this way means that the hand can be used for normal operation without associated ligament fatigue, without compromising the tunnel dimension and without endangering the healing process.

Obviously, minor changes may be made in the form and construction of this invention without departing from its spirit. Thus, it is not desired to confine the invention to the exact form shown and described, but it is desire to include all such as properly come within the scope claimed.

The invention having thus been described, what is claimed as new and desired to secure by Letters Patent is:

1. An improved splint system for the treatment and prevention of carpel tunnel syndrome in the wrist of a human being, said wrist having a radius, an ulna and first and second narrow sides, said splint system comprising:

(a) a substantially V-shaped brace of semi-rigid material consisting of a pair of generally planar panels joined along a corner and diverging therefrom to provide a first free end and a second free end, said panels being dimensioned and angularly oriented to embrace a first narrow side of the wrist of a human being;

(b) a strap connected to one of said free ends of said brace and dimensioned to extend about the second narrow side of the wrist;

(c) means on the other of said free ends for engagement by said strap; and (d) means for securing said strap in an adjusted length between said free ends to cooperate with said brace to apply pressure upon the opposite narrow sides of the wrist of the patient to press the radius and ulna of the wrist toward one another, said brace retaining its V-shaped configuration when said splint system is secured about the wrist of the patient.

2. The improved splint system as recited in claim 1, wherein the semi-rigid material of said brace is a thermoplastic resin.

3. The improved splint system as recited in claim 1, wherein said corner is rounded.

4. The improved splint system as recited in claim 1, wherein said strap is of a generally elongated rectangular configuration and wherein said securing means is a hook-and-loop fastener system.

5. The improved splint system as recited in claim 1, wherein each panel has an aperture adjacent its free end through which said strap extends.

6. The improved splint system as recited in claim 5, wherein said strap has a loop at one end fastened in the aperture of one panel, and slidably extends through the aperture in the other of said panels, and wherein said strap is releasably fastened to itself by said securing means.

7. The improved splint system as recited in claim 1, wherein the inner surface of said brace is provided with a cushion of a resilient polymeric material.

8. A method of treating and preventing carpal tunnel syndrome in the wrist of a human being, said wrist having a radius, an ulna, and first and second narrow sides, comprising:

(a) providing a splint system including a substantially V-shaped brace of semi-rigid material, consisting of a pair of generally planar panels joined along a corner and diverging therefrom with a first free end and a second free end, and at least one strap extensible between said free ends, wherein the method comprises:

(b) placing said brace to embrace the first narrow side of the wrist of a human being;

(c) extending said strap about the second narrow side of said wrist between said free ends; and (d) adjusting said strap so that said strap and brace bear upon opposite sides of said wrist to press said radius and ulna of the wrist toward one another.

* * * * *